United States Patent
Zhang et al.

(10) Patent No.: US 9,924,894 B2
(45) Date of Patent: Mar. 27, 2018

(54) NON-INVASIVE MEASUREMENT OF SKIN THICKNESS AND GLUCOSE CONCENTRATION WITH RAMAN SPECTROSCOPY AND METHOD OF CALIBRATION THEREOF

(71) Applicant: Hong Kong Applied Science and Technology Research Institute Co. Ltd., Shatin, New Territories (HK)

(72) Inventors: Chun Zhang, Hong Kong (HK); Tsz Ho Lau, Hong Kong (HK); Yuk Cheung Chan, Hong Kong (HK); Wei Mong Tsang, Hong Kong (HK)

(73) Assignee: Hong Kong Applied Science and Technology Research Institute Co. Ltd., Hong Kong (CN)

( * ) Notice: Subject to any disclaimer, the term of this patent is extended or adjusted under 35 U.S.C. 154(b) by 540 days.

(21) Appl. No.: 14/729,075

(22) Filed: Jun. 3, 2015

(65) Prior Publication Data
US 2016/0354015 A1    Dec. 8, 2016

(51) Int. Cl.
*A61B 5/1455*    (2006.01)
*A61B 5/145*    (2006.01)
*A61B 5/107*    (2006.01)
*A61B 5/00*    (2006.01)
(Continued)

(52) U.S. Cl.
CPC .......... *A61B 5/1455* (2013.01); *A61B 5/0075* (2013.01); *A61B 5/1075* (2013.01); *A61B 5/1076* (2013.01); *A61B 5/1079* (2013.01); *A61B 5/1495* (2013.01); *A61B 5/14532* (2013.01); *A61B 5/7225* (2013.01); *A61B 5/7246* (2013.01); *A61B 5/7275* (2013.01);
(Continued)

(58) Field of Classification Search
CPC ... A61B 5/0059; A61B 5/0205; A61B 5/1455; A61B 5/14551; A61B 5/14552; A61B 5/14532; A61B 5/1495; A61B 5/72; A61B 5/7225; A61B 5/7246; A61B 5/7275; A61B 5/7278
See application file for complete search history.

(56) References Cited

U.S. PATENT DOCUMENTS

| | | | |
|---|---|---|---|
| 5,615,673 | A | 4/1997 | Berger et al. |
| 6,280,381 | B1 | 8/2001 | Malin et al. |
| 6,456,870 | B1 | 9/2002 | Rennert et al. |

(Continued)

FOREIGN PATENT DOCUMENTS

| | | |
|---|---|---|
| CN | 101253396 | 8/2008 |
| WO | WO2013096856 | 6/2013 |

*Primary Examiner* — Eric Winakur
*Assistant Examiner* — Chu Chuan (JJ) Liu
(74) *Attorney, Agent, or Firm* — Eagle IP Limited; Jacqueline C. Lui

(57) ABSTRACT

The present invention discloses a non-invasive method of measuring skin thickness and blood glucose concentration of a subject by a Raman system. The advantage of the present invention is that a single Raman spectrum is used to measure both the skin thickness and glucose concentration. The skin thickness and Raman intensity retrieved from the same Raman spectrum are both utilized to yield a more accurate blood glucose concentration. The present invention also discloses a Raman system for measuring physiological data of a subject. It comprises a Raman spectroscopic unit and a signal processing unit.

22 Claims, 10 Drawing Sheets

(51) Int. Cl.
  *A61B 5/1495* (2006.01)
  *A61B 5/05* (2006.01)
(52) U.S. Cl.
  CPC .......... *A61B 5/7278* (2013.01); *A61B 5/0507* (2013.01); *A61B 2562/0238* (2013.01)

(56) References Cited

U.S. PATENT DOCUMENTS

| | | |
|---|---|---|
| 6,671,542 B2 | 12/2003 | Rennert et al. |
| 7,647,092 B2 | 1/2010 | Motz et al. |
| 7,862,507 B2 | 1/2011 | Crowther et al. |
| 8,355,767 B2 | 1/2013 | Hunter et al. |
| 8,553,219 B2 | 10/2013 | Patil et al. |
| 2006/0200017 A1* | 9/2006 | Monfre .............. A61B 5/14532 600/344 |
| 2006/0211926 A1 | 9/2006 | Yu |
| 2007/0049809 A1 | 3/2007 | Bechtel et al. |
| 2012/0035442 A1 | 2/2012 | Barman et al. |
| 2013/0018237 A1 | 1/2013 | Henneberg et al. |
| 2016/0128612 A1* | 5/2016 | Cho .................... A61B 5/1455 600/316 |
| 2016/0356720 A1* | 12/2016 | Van Dorpe .......... A61B 5/1455 |

\* cited by examiner

NON-INVASIVE MEASUREMENT OF SKIN THICKNESS AND GLUCOSE CONCENTRATION WITH RAMAN SPECTROSCOPY AND METHOD OF CALIBRATION THEREOF

FIELD OF INVENTION

This invention relates to the measurement of blood analytes, and in particular the non-invasive measurement of blood glucose concentration based on Raman spectroscopy.

BACKGROUND OF INVENTION

Raman spectroscopy is a powerful tool for quantitative analysis of the composition and concentration of blood analytes within a sample, such as blood glucose 15 concentration. Raman spectroscopy is based on inelastic light scattering rather than absorption of light. Interactions between the incident photons and molecules in the sample result in scattering of light. Comparing with many other techniques, Raman is a sensitive and selective technique. It can measure glucose at a very low concentration in a test tube. However, when it comes to non-invasive measurement of glucose in human 20 body, the result is unreliable due to the variations and fluctuations in the subject's physiological state and other environmental factors. There have been many attempts to improve the sensitivity and accuracy of blood glucose measurement based on Raman system. Even though the best sensitivity achieved so far is getting close to 15 mg/dl in human body that can only be obtained after tedious calibration procedures associated 25 with multivariate analysis without specifying the origins of the variations in the Raman spectra. As a result, the stability of such calibration procedures and the robustness of such glucose predictions are often questionable.

Therefore, a better approach is called for to circumvent above-mentioned shortcomings.

SUMMARY OF INVENTION

In the light of the foregoing background, it is an object of the present invention to provide an alternate approach to measure blood glucose concentration of a subject with improved sensitivity and accuracy in a non-invasive environment.

Accordingly, the present invention, in one aspect, provides a method of operating a physiological measurement system for measuring the skin thickness and blood glucose concentration based on the same Raman spectrum from the target subject. The Raman signal is first collected from a predetermined area of a subject's skin with an epidermis layer named first layer and dermis layer named second layer. The Raman signal is then processed to obtain a first data relating to the thickness of the first layer and a second data relating to the glucose concentration within the second layer. Finally, the blood glucose concentration is calculated based on the first data and the second data.

In one embodiment, the thickness of the first layer is obtained by: calculating a ratio of two intensities at the pre-determined signal wavenumber and reference wavenumber; and referring to a pre-stored ratio vs. skin thickness curve in the Raman system to determine the skin thickness according to a first prediction model. In one embodiment, the signal wavenumber is within 1300 $cm^{-1}$ to 1340 $cm^{-1}$ and the reference wavenumber is within 1440 $cm^{-1}$ to 1460 $cm^{-1}$.

In a further embodiment, the pre-stored ratio vs. skin thickness curve in the Raman system is determined by: a) collecting a plurality of aforementioned ratios at different body locations of at least one subject; b) measuring skin thickness for each body location by an invasive reference method or a non-invasive reference method such as optical coherence tomography method, ultrasound imaging method, Terahertz imaging method, and near-infrared absorption; c) generating the ratio vs. skin thickness curve correlating the ratio to the skin thickness for each body location; and d) determining a first set of constants from the calibration curve.

In an exemplary embodiment of the present invention, the second data relating to the glucose concentration of the second layer is computed from at least one intensity of the Raman signal, each intensity corresponding to at least one prespecified wavenumber of the Raman signal. The prespecified wavenumber is within the range of 800 $cm^{-1}$ to 1500 $cm^{-1}$. The final glucose concentration in the blood is calculated based on the first data, the second data and a second prediction model. The second prediction model further has a second set of constants which are determined by a second calibration.

According to one aspect of the present invention the blood glucose concentration is calculated based on absolute skin thickness of the target subject. The second data is at least one intensity of the Raman signal. The glucose concentration in the blood is calculated based on a second prediction model, which comprises a functional relationship correlating the glucose concentration with the absolute skin thickness and the Raman intensity.

According to another aspect of the present invention the blood glucose concentration is calculated based on relative skin thickness of the target subject. The second data is at least one intensity of the Raman signal. The glucose concentration in the blood is calculated based on a second prediction model, which comprises a functional relationship correlating the glucose concentration with the relative skin thickness and the Raman intensity. The relative skin thickness is the difference between the skin thickness and a skin thickness mean value.

In one embodiment, the skin thickness mean value is obtained by averaging at least two values of skin thickness obtained from substantially the same body location of same subject.

According to another aspect of the present invention the blood glucose concentration is calculated based on absolute Raman ratio for the skin thickness of the target subject. The second data is at least one intensity of the Raman signal. The glucose concentration in the blood is calculated based on a second prediction model, which comprises a functional relationship correlating the glucose concentration with the absolute Raman ratio and the Raman intensity.

According to another aspect of the present invention the blood glucose concentration is calculated based on relative Raman ratio for the skin thickness of the target subject. The second data is at least one intensity of the Raman signal. The glucose concentration in the blood is calculated based on a second prediction model, which comprises a functional relationship correlating the glucose concentration with the relative Raman ratio and the Raman intensity. The relative Raman ratio is the difference between the Raman ratio for the skin thickness and a Raman ratio mean value.

In one embodiment, the Raman ratio mean value is obtained by averaging at least two values of Raman ratio for the skin thickness obtained from substantially the same body location of same subject.

The second prediction model which comprises a second set of constants is obtained by a second calibration by: a) measuring a plurality of blood glucose concentrations over a time course at a predetermined body location from same subject by a reference method such as commercially available glucose meter; b) concurrently, collecting a plurality of Raman spectra from the predetermined body location of the same subject; c) deriving at least one group of variables from each Raman spectrum; and d) determining the values of the second set of constants for the subject based on the second prediction model and the plurality of blood glucose concentrations obtained in the first step and those variables.

In another aspect of the present invention, a physiological measurement system for measuring physiological data of a subject at a predetermined area is also provided. The system comprises of a Raman spectroscopic unit and a signal processing unit. The Raman spectroscopic unit comprises of an excitation light source that illuminates an optical signal into the predetermined area of the subject's skin; and an optical detector that receives a Raman signal reflected from the predetermined area of the subject's skin. The signal processing unit comprises of a microprocessor coupled to the optical detector; and a computer-readable storage medium coupled to the microprocessor. The computer-readable storage medium is encoded with computer-readable codes to instruct the microprocessor to execute the following steps: acquiring a first data relating to the skin thickness of the epidermis layer from the Raman signal; acquiring a second data relating to the glucose concentration from the Raman signal; computing the skin thickness of the epidermis layer based on the first data and a first prediction model; and computing the glucose concentration based on the skin thickness of the epidermis layer, the second data, and a second prediction model.

In another aspect of the present invention, a method of operating a physiological measurement system for measuring the thickness of a predetermined area of a subject's skin is provided. A Raman signal is first collected from a predetermined area. Then a first predetermined wavenumber and a second predetermined wavenumber are identified. The intensities of the Raman signal at the first predetermined wavenumber and the second predetermined wavenumber are then retrieved and a ratio of the two intensities is calculated. Finally, the thickness of the predetermined area of the subject's skin is determined based on the calculated ratio and a prediction model. The prediction model in this case comprises a functional relationship among a plurality of attributes correlating the thickness of the predetermined area and the ratio.

In an exemplary embodiment of the present invention, the first predetermined wavenumber and the second predetermined wavenumber are determined by: a) measuring a plurality of skin thicknesses at a plurality of body locations from a plurality of subjects by an invasive reference method or a non-invasive reference method such as optical coherence tomography method, ultrasound imaging method, Terahertz imaging method, and near-infrared absorption; b) obtaining the corresponding Raman spectrum of each body location, the Raman spectrum comprising a plurality of signals with wavenumber ranging from 300 $cm^{-1}$ to 1800 $cm^{-1}$; c) selecting a first set of wavenumbers sensitive to skin characteristic composition of the body locations and a second set of wavenumbers insensitive to skin characteristic composition of the body locations; d) selecting a first wavenumber from the first set and a second wavenumber from the second set; e) retrieving a first intensity from the Raman spectrum at the first wavenumber and a second intensity from the Raman spectrum at the second wavenumber; f) calculating a Raman ratio of the first intensity and the second intensity for each Raman spectrum; g) repeating step d-f for all combinations of the first wavenumber and the second wavenumber; h) for each first wavenumber and each second wavenumber, identifying a set of candidate wavenumber pairs wherein in each candidate wavenumber pair, the Raman ratios and the skin thicknesses of the plurality of subjects conform to a generic functional relationship; i) determining an optimal wavenumber pair among set of candidate wavenumber pairs that yields most compact representation of the generic functional relationship; and j) assigning the first wavenumber and the second wavenumber in the optimal wavenumber pair as the first predetermined wavenumber and the second predetermined wavenumber respectively.

In another embodiment, the identifying step further includes the steps of: identifying a cluster of points for each body location on the Raman ratio vs. skin thickness plot and computing a cluster center for each cluster. Those candidate wavenumber pairs wherein the cluster centers fit a generic functional relationship are retained and the candidate wavenumber pair yielding the most compact representation is selected as the optimal pair.

There are many advantages to the present invention. An advantage is that a single Raman spectrum is used to determine both the skin thickness and glucose concentration. The skin thickness data and measured Raman intensity retrieved from the same Raman spectrum are both utilized to yield a more accurate blood glucose concentration. This is advantageous as the skin thickness and Raman intensity are measured at the same body location at the same time; thus eliminating any positional uncertainty and simplifying the measurement procedure. Another advantage of the present invention is that calibration parameters acquired under certain circumstances may be re-used within specific time period and can be applied to subsequent measurements without sacrificing the measurement accuracy.

DETAILED DESCRIPTION OF THE PREFERRED EMBODIMENTS

Figure 1:
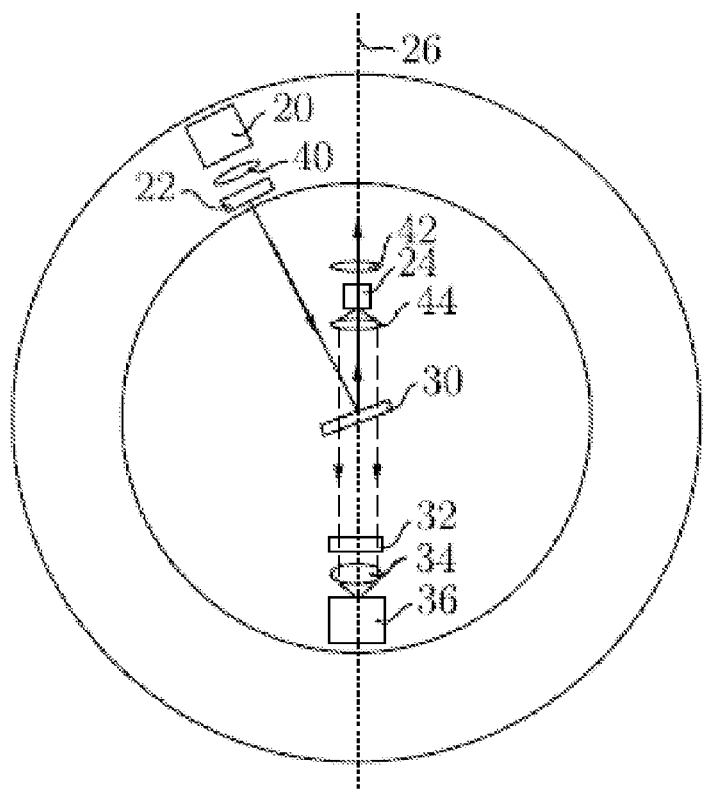
FIG. 1 is a schematic diagram of a Raman system for the collection of Raman signals.

As used herein and in the claims, "comprising" means including the following elements but not excluding others. "Couple" refers to electrical coupling either directly or indirectly via one or more electrical means unless otherwise stated.

The embodiments described herein disclose inventive ideas of capturing and analyzing physiological data of a subject and can be implemented in a number of different ways. In particular, four approaches based on absolute skin thickness and relative skin thickness are described below. Based on the teaching of this disclosure, other configurations or variations can also be realized by those skilled in the art but they would still fall in the scope of the present invention.

When an excitation light irradiates an analyte, at least some of the light will be scattered by the analyte. The scattered radiation may include Raman-scattered radiation. The characteristics of the Raman-scattered radiation provide information relating to the analyte. As used herein, the Raman-scattered radiation that is scattered by the analyte is referred to as the "Raman signal". The Raman-scattered radiation that is scattered by glucose molecules is referred to as the "Glucose signal". The term "Raman spectrum" refers to a plot of the intensity of Raman signal versus Raman shift. "Raman shift" is usually expressed in wavenumber ($cm^{-1}$) and represents the difference in the absolute wavenumber of the peak and the wavenumber of the excitation light. The term "Raman intensity" refers to the intensity of the Raman signal.

Non-invasive Raman measurement probes glucose molecules in extracellular fluids, including interstitial fluid (or tissue fluid) and blood, of human body. Such extracellular fluids distribute unevenly across the skin. In a simplified model, we consider the skin having two layers: a top layer named epidermis and a bottom layer named dermis. The glucose signal is generated from the glucose molecules in the bottom layer and attenuated by the top layer. The thickness of the epidermis varies over different locations of the human body. As a result, the measured glucose signal varies across different locations. As such, in order to accurately predict blood glucose concentration of a certain subject, the corresponding skin thickness must be determined to correct the obtained Raman signal by compensating the attenuation.

Raman intensity of skin contains many peaks in its Raman spectrum. They are either from the top layer or the bottom layer, or a combination of both. For certain wavenumbers, the Raman peaks varies widely according to skin thickness. This is because the Raman signals at these wavenumbers arise from the molecules at the top layer and can be called signal peaks as they are a characteristic of the thickness of the top layer. For other wavenumbers, the Raman peaks are insensitive to skin thickness as these peaks are generated by common molecules in both top and bottom layers. Such Raman peaks are called reference peaks. In order to identify the characteristic signal peaks and reference peaks, numerous Raman spectra for different body locations of different people were measured by using a Raman system in reflectance mode.

In one embodiment, a Raman system as shown in FIG. 1 is used to collect the Raman signals and Raman peaks as mentioned above. The Raman system comprises a Raman spectroscopic unit and a signal processing unit. The Raman spectroscopic unit includes an excitation light source 20, a sample holder 24 and a detector 36 coupled to a frame (coupling not shown for ease of illustration). A line filter 22 is positioned in front of the excitation light source 20. In one embodiment, the laser source 20 is a 1064 nm diode pump solid state continuous wave laser operated at 450 mW. The center wavelength of the line filter 22 is at 1064 nm with a Full-Width Half Maximum (FWHM) value of 10 nm. A first notch filter 30, a second notch filter 32 and a lens 34 are aligned respectively in this order between the sample holder 24 and the detector 36 along the signal axis 26, with the lens 34 positioned closest to the detector 36. In one embodiment, the first notch filter 30 and the second notch filter 32 reflect light of wavelength centered at 1064 nm with FWHM of 40 nm Hence, they reflect a narrow band of ±20 nm of the center wavelength 1064 nm while transmit light in all other wavelengths. A collimator 40 is positioned between the excitation light source 20 and the line filter 22. A first lens 42 and a second lens 44 are positioned on two sides of the sample holder 24 along the signal axis 26. In one embodiment, the first lens 42 and the second lens 44 are 1-inch BK7 lens with focal length ranging from 1 to 2 inches. During operation, the collimator 40 collimates the excitation light generated from the excitation light source 20 to the first notch filter 30. The first notch filter 30 reflects the excitation light to the sample in a second direction along the signal axis 26 for generating reflectance Raman signal. The second lens 44 directs the reflectance Raman signal generated from the sample to the detector 36 via the first notch filter 30, the second notch filter 32 and the lens 34. The signal processing unit (not shown in FIG. 1) comprises a microprocessor coupled to the detector 36 and a computer-readable storage medium coupled to the microprocessor. The computer-readable storage medium is encoded with computer-readable codes to instruct the microprocessor to acquire data from the detector 36 and perform data processing which will be discussed in details below.

Figure 2:
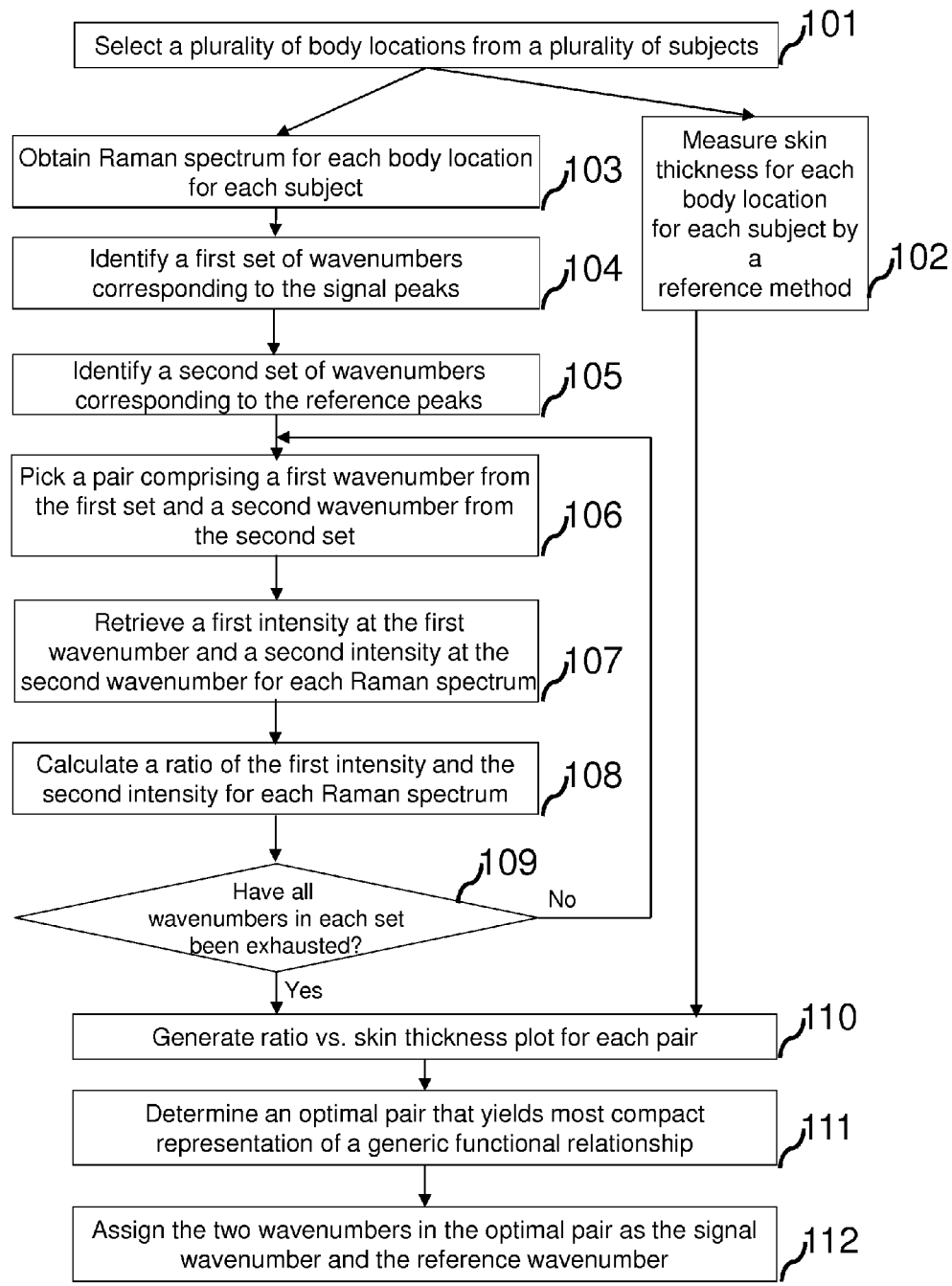
FIG. 2 is a flow chart for identifying the signal wavenumber and the reference wavenumber according to an embodiment of the present invention.

In an exemplary embodiment, a flow chart for identifying the signal wavenumber and the reference wavenumber is shown in FIG. 2. In step 101, a plurality of subjects and a plurality of body locations are selected. Each Raman spectrum, comprising a plurality of signals with wavenumbers ranging from 300 $cm^{-1}$ to 1800 $cm^{-1}$, corresponds to a different skin thickness as they are obtained from different body locations on different subjects. The skin thickness for each location of each subject is measured by a reference method such as the Optical Coherent Tomography (OCT), ultrasound imaging, Terahertz imaging, and near-infrared absorption spectroscopy in step 102. After obtaining the Raman spectra in step 103, the Raman peaks are first identified as signal peaks and reference peaks. Those wavenumbers corresponding to signal peaks are grouped together to form a first set in step 104 and those corresponding to reference peaks are collected to form a second set in step 105. In step 106, a pair of wavenumbers, one from the first set and another from the second set, is picked. Their respective Raman intensities are retrieved in step 107 and the ratio between the first intensity of the first wavenumber from the first set and the second intensity of the second wavenumber from the second set is calculated in step 108. Step 109 checks whether all possible pairs of wavenumbers, one from the first set and the other from the second set are processed. If not, then steps 106 to 108 are repeated for another pair. After collecting all the ratios for all the pairs, a ratio vs. skin thickness plot is created for each body position among all subjects in step 110. Then an optimal pair that yields most compact representation of a generic functional correlation between the Raman ratio and the skin thickness is identified in step 111. The identifying step 111 further includes the steps of: identifying a cluster of data points for each body location on the ratio vs. skin thickness plot and computing a cluster center for each cluster. Those candidate wavenumber pairs wherein the cluster centers fit a generic functional relationship are retained and the candidate wavenumber pair yielding the most compact representation is selected as the optimal pair. In one embodiment, the candidate wavenumber pair that yields the minimum aggregated standard deviations is chosen. In the last step 112, the corresponding wavenumbers in the optimal pair are assigned as the signal wavenumber that is most sensitive to the thickness of epidermis layer and the reference wavenumber that is insensitive to the thickness variation.

After extensive measurements and data processing, the signal wavenumber is identified to be within 1300 cm$^{-1}$ to 1340 cm$^{-1}$. The reference wavenumber is identified to be within 1440 cm$^{-1}$ to 1460 cm$^{-1}$. In one embodiment, the signal wavenumber is at 1321 cm$^{-1}$, and the reference wavenumber is at 1446 cm$^{-1}$.

Referring now to the generic functional relationship mentioned above. The glucose signal is generated from the glucose molecules in the dermis layer and attenuated by the epidermis layer. At depth $\xi$ inside epidermis, Raman intensity generated from d$\xi$ is $$dS_{signal}' = aI_{excitation}' \quad (1)$$

where a is a constant proportional to Raman activity, $I_{excitation}'$ is the intensity of the excitation light at depth $\xi$. The initial excitation light $I_{excitation}$ and Raman signal generated from d$\xi$ are attenuated as they travel across the epidermis. The attenuated intensity is described as $$I_{excitation}' = I_{excitation} e^{-\frac{\xi}{\lambda}} \quad (2)$$

$$dS_{signal} = dS_{signal}' e^{-\frac{\xi}{\lambda}} \quad (3)$$

Substituting equation (2) and (3) back to (1), $$dS_{signal} = aI_{excitation} e^{-\frac{2\xi}{\lambda}} \quad (4)$$

Sum up the contributions across the whole epidermis with a thickness of z $$S_{signal} = \int_0^z aI_{excitation} e^{-\frac{2\xi}{\lambda}} d\xi = \frac{a\lambda I_{excitation}}{2}(1 - e^{-\frac{2z}{\lambda}}) \quad (5)$$

The ratio of Raman intensity at the signal wavenumber and the reference wavenumber is $$r = \frac{S_{signal}}{S_{reference}} = \frac{a\lambda I_{excitation}}{2S_{reference}}(1 - e^{-\frac{2z}{\lambda}}) = R_{EP}(1 - e^{-\frac{2z}{\lambda}}) \quad (6)$$

As $S_{signal}$ may not arise from epidermis solely, an offset term $R_0$ is added to account for other factors $$r = R_{EP}(1 - e^{-\frac{2z}{\lambda}}) + R_0 \quad (7)$$

Equation (7) is the first prediction model for determining skin thickness. $R_{EP}$, $\lambda$ and $R_0$ are a first set of constants obtained from a first calibration and the least squares curve fitting. By applying this first prediction model, skin thickness is determined through a mapping of relative ratios of characteristic peaks in Raman spectrum.

Figure 3:
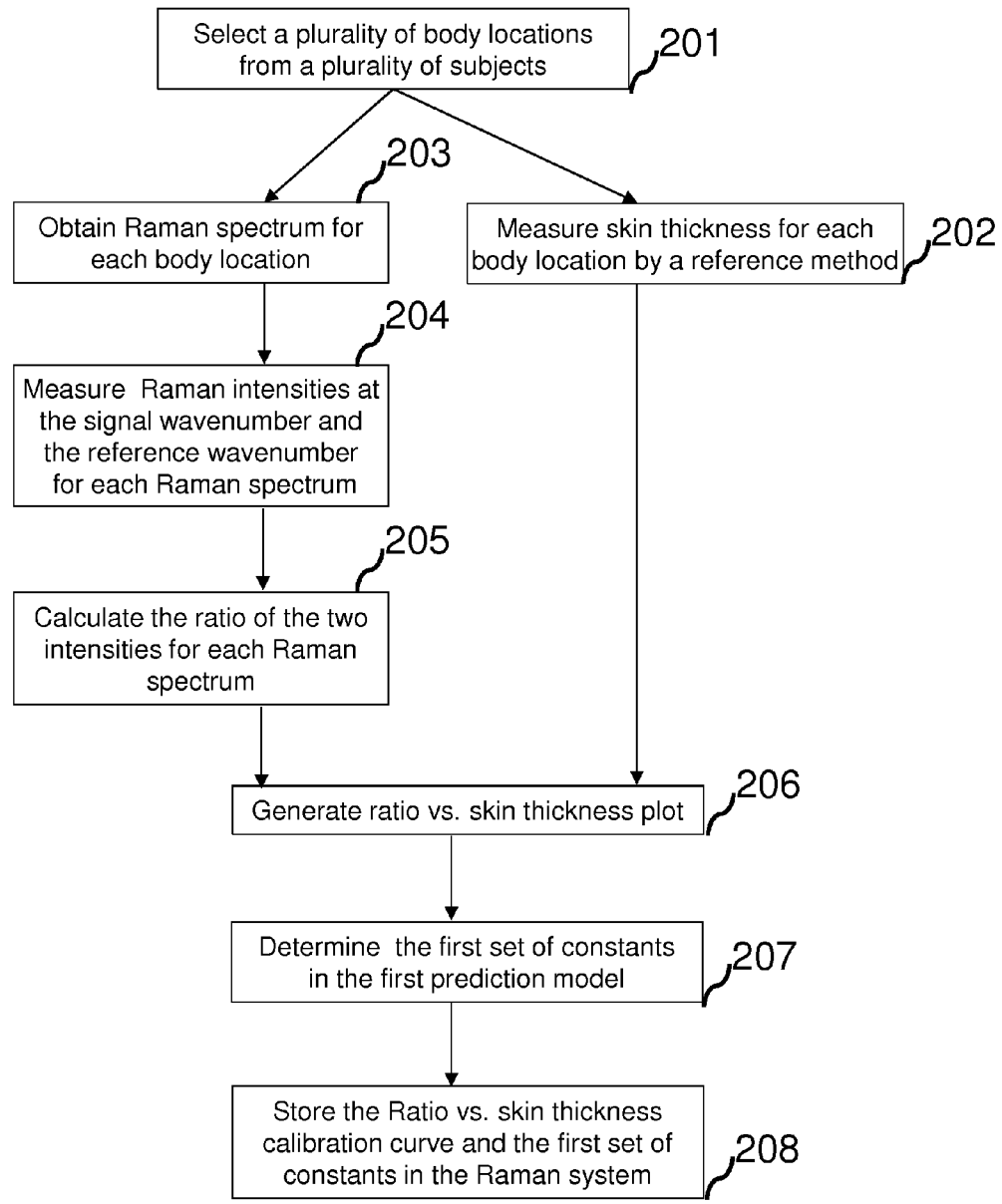
FIG. 3 is a flow chart for the first calibration procedure according to an embodiment of the present invention.

In an exemplary embodiment, a flow chart for the first calibration procedures is shown in FIG. 3. In step 201, a plurality of subjects and a plurality of body locations are selected. The thickness of each location can be measured by any reference method such as Optical Coherent Tomography (OCT), ultrasound imaging, Terahertz imaging, and near-infrared absorption spectroscopy in step 202. After obtaining Raman spectrum from each body location by the Raman system of the present invention in step 203, the Raman intensities at the signal wavenumber and the reference wavenumber are retrieved from each Raman spectrum in step 204. After that, the ratio of the two intensities for each Raman spectrum is calculated in step 205. Then ratio vs. skin thickness data for each body location is registered on the same graph in step 206. In step 207, a calibration curve based on the first prediction model is fitted and the first set of constants $R_{EP}$, $\lambda$ and $R_0$ is extracted by the least squares curve fitting. At last, the ratio vs. skin thickness calibration curve and the first set of constants are stored in the Raman system in step 208.

Figure 4:
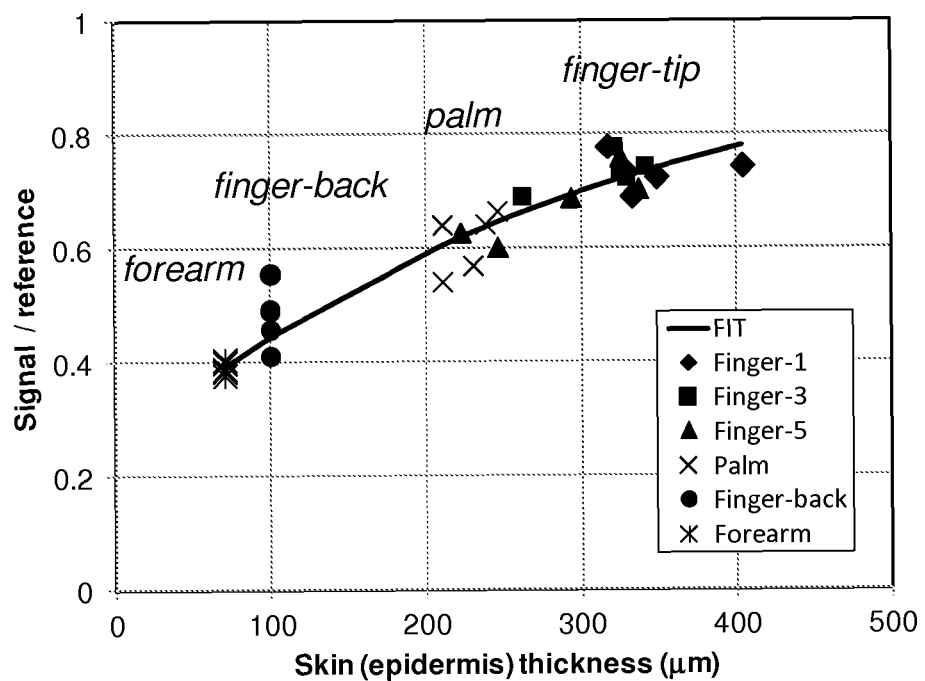
FIG. 4 is an exemplary ratio vs. skin thickness calibration curve according to an embodiment of the present invention.

In an exemplary embodiment of the present invention, a ratio vs. skin thickness calibration curve is shown in FIG. 4. It is generated from thirty data points from six body locations of five subjects. The signal/reference ratio of the Raman intensity was calculated at 1321 cm$^{-1}$ (the signal wavenumber) and 1446 cm$^{-1}$ (the reference wavenumber) from each Raman spectrum. The skin thickness of each body location was measured by Terahertz imaging. The calibration curve is fitted based on the first prediction model.

Figure 5A:
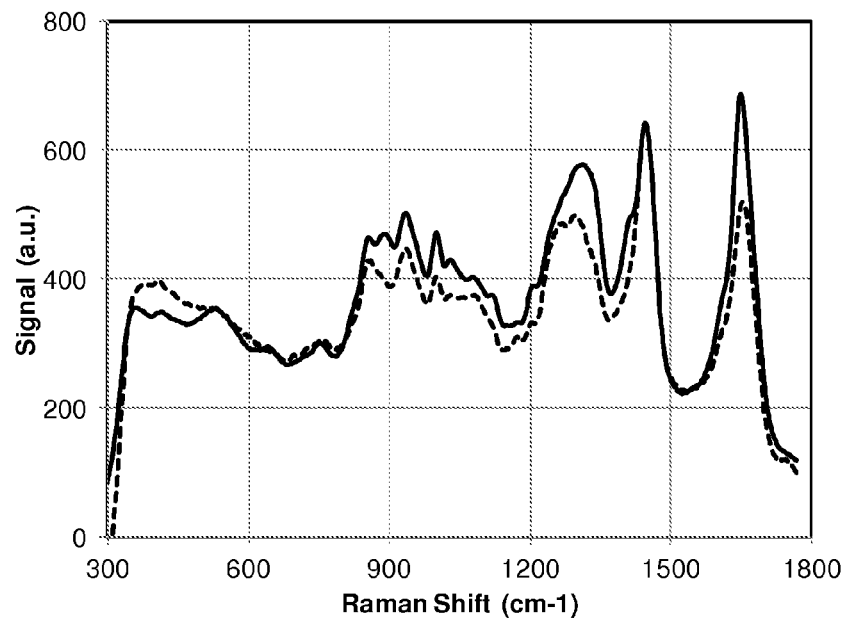
FIG. 5A plots exemplary Raman spectra obtained from a fingertip (solid line) and from a forearm (dash line) of a subject.
Figure 5B:
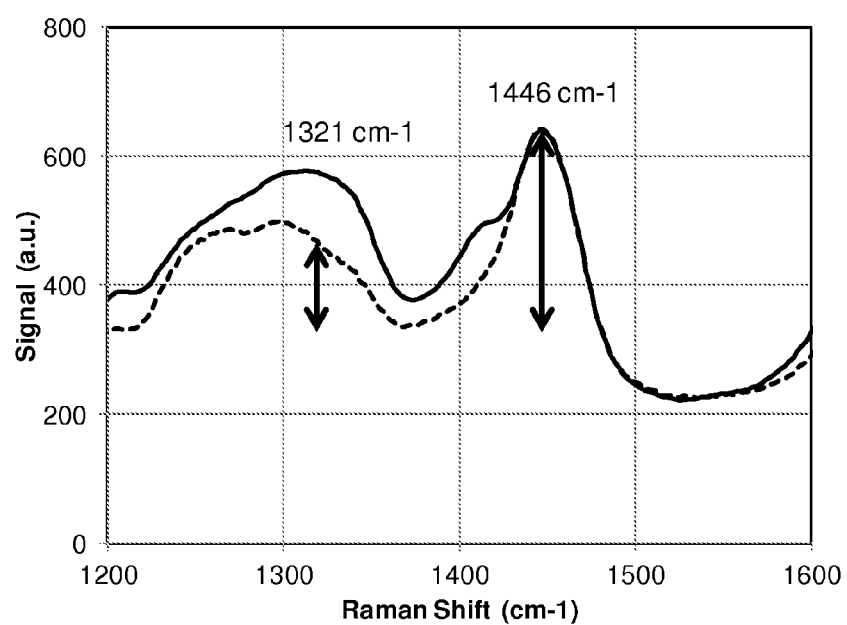
FIG. 5B is a zoom-in figure of FIG. 5A, showing the Raman intensities at the signal wavenumber and the reference wavenumber.

FIG. 5A plots exemplary Raman spectra obtained from a fingertip and from a forearm of a subject. Both Raman spectra were obtained using the above-mentioned Raman system. Each Raman spectrum, comprising a plurality of signals with wavenumbers ranging from 300 cm$^{-1}$ to 1800 cm$^{-1}$, corresponds to a skin thickness value to be determined. By calculating the ratio of Raman intensity at 1321 cm$^{-1}$ and 1446 cm$^{-1}$ for each spectrum as shown in the zoom-in figure of FIG. 5B, and then referring to the ratio vs. skin thickness calibration curve, the subject's skin thickness at fingertip and forearm can be determined.

Moreover, each Raman spectrum, comprising a plurality of signals with wavenumbers ranging from 300 cm$^{-1}$ to 1800 cm$^{-1}$, corresponds to a glucose concentration value to be determined. The present invention discloses four approaches of determining blood glucose concentration using a second prediction model. In different approaches, different equations are used in the second prediction model.

At one specific wavenumber, the intensity of Raman signal is:

$$S_i = S_{i,G} + S_{i,E} + S_{i,0} \quad (8)$$

where $S_i$ is the intensity of Raman signal measured, $S_{i,G}$ is the intensity of Raman signal contributed by the glucose molecules in dermis, $S_{i,E}$ is the intensity of Raman signal contributed by epidermis, and $S_{i,0}$ is an offset constant accounting for the signals from other sources which is independent of the skin thickness of epidermis. As epidermis is acting as an optical attenuation layer for glucose Raman signal from dermis, $S_{i,G}$ can be describes as:

$$S_{i,G} \propto v C_G e^{-\frac{2z}{\lambda}} \quad (9)$$

where $C_G$ is glucose concentration at the interstitial body fluid in the dermis, v is the volume fraction of the interstitial body fluid in the dermis, z is the thickness of epidermis, $\lambda$ is the optical penetration depth of epidermis.

Referring to equation (5), Raman signal contributed by epidermis $S_{i,E}$ can be describes as:

$$S_{i,E} \propto (1 - e^{-\frac{2z}{\lambda}}) \quad (10)$$

Substituting equation (9) and (10) back to equation (8), $S_i$ is rewritten as:

$$S_i = \alpha_i v C_G e^{-\frac{2z}{\lambda}} + \beta_i (1 - e^{-\frac{2z}{\lambda}}) + S_{i,0} \quad (11)$$

where $\alpha_i$ and $\beta_i$ are constants.

Approach 1 Based on Absolute Skin Thickness

From equation (11), the glucose concentration is given by $$C_G = \frac{S_i}{\alpha_i v}(e^{\frac{2z}{\lambda}}) - \frac{\beta_i}{\alpha_i v}(e^{\frac{2z}{\lambda}} - 1) - \frac{S_{i,0}}{\alpha_i v}(e^{\frac{2z}{\lambda}}) \quad (12)$$

For the whole Raman spectrum in the processing range mentioned above, the glucose concentration is calculated as a weighted average of the contribution from all wavenumbers.

$$C_G = \Sigma_i w_i \left[ \frac{S_i}{\alpha_i v}(e^{\frac{2z}{\lambda}}) - \frac{\beta_i}{\alpha_i v}(e^{\frac{2z}{\lambda}} - 1) - \frac{S_{i,0}}{\alpha_i v}(e^{\frac{2z}{\lambda}}) \right] \quad (13)$$

where $$\Sigma_i w_i = 1 \quad (14)$$

Let $$C_{i,SS} = \frac{w_i}{\alpha_i v}, \; C_{EP} = -\Sigma_i \frac{w_i \beta_i}{\alpha_i v}, \text{ and } C_{G0} = -\Sigma_i \frac{w_i S_{i,0}}{\alpha_i v} \quad (15)$$

Equation (13) can then be rewritten as $$C_G = \Sigma_i C_{i,SS} S_i (e^{\frac{2z}{\lambda}}) + C_{EP}(e^{\frac{2z}{\lambda}} - 1) + C_{G0}(e^{\frac{2z}{\lambda}}) \quad (16)$$

Equation (16) is the second prediction model for determining the blood glucose concentration, where $\lambda$ is a constant parameter obtained from a first calibration as described in FIG. 3. $C_{i,SS}$, $C_{EP}$ and $C_{G0}$ are constants to be determined by a second calibration for a specific location of an individual subject within a specific time period. In one embodiment, they are obtained by applying techniques such as multiple linear regressions, partial least squares regression or other techniques using a calibration dataset containing the variables: $C_G$, $S_i$, and z. The blood glucose concentration $C_G$ is determined by equation (16) based on the absolute skin thickness z and the measured Raman intensity $S_i$, both of which can be retrieved from the same Raman spectrum obtained from a certain body location.

Approach 2 Based on Relative Skin Thickness

The thickness of epidermis z can be further described as $$z = z_0 + \Delta z \quad (17)$$

where $z_0$ is the mean epidermis thickness, a constant. Within a small body region, $\Delta z$ is much smaller than $\lambda$ ($\Delta z \ll \lambda$, e.g., 50 µm as compared to 1000 µm). By first order approximation, $$e^{\frac{2z}{\lambda}} = e^{\frac{2z_0}{\lambda}}\left(1 + \frac{2\Delta z}{\lambda}\right) \quad (18)$$

Substituting equation (18) into equation (16), then:

$$C_G = C_0 + \Sigma_i C_{i,S} S_i + \Sigma_i C_{i,SZ}(S_i \Delta z) + C_Z \Delta z \quad (19)$$

where $C_0 = (C_{EP} + C_{G0})(e^{\frac{2z_0}{\lambda}}) - C_{EP}$, $$C_{i,S} = C_{i,SS}\left(e^{\frac{2z_0}{\lambda}}\right), \; C_{i,SZ} = \frac{2C_{i,SS}}{\lambda}\left(e^{\frac{2z_0}{\lambda}}\right), \text{ and}$$

$$C_Z = \frac{2(C_{EP} + C_{G0})}{\lambda}\left(e^{\frac{2z_0}{\lambda}}\right) \quad (20)$$

$C_0$, $C_{i,S}$, $G_{i,SZ}$, and $C_Z$ are constants to be determined by a second calibration for a specific location of an individual subject within a specific time period. In one embodiment, they are determined by applying techniques such as multiple linear regressions, partial least squares regression or other techniques using a calibration dataset containing the variables: $C_G$, $S_i$, and $\Delta z$.

Approach 3 Based on Absolute Raman Ratio

As the thickness of epidermis z is closely related to the characteristic Raman peak ratio r, the glucose concentration $C_G$ can be determined without deriving the exact values of the skin thickness z. From equation (7) and equation (16), $$C_G = \quad (21)$$

$$\Sigma_i C_{i,SS} S_i \left(\frac{R_{EP}}{R_{EP} + R_0 - r}\right) + C_{EP}\left(\frac{r - R_0}{R_{EP} + R_0 - r}\right) + C_{G0}\left(\frac{R_{EP}}{R_{EP} + R_0 - r}\right)$$

$R_{EP}$ and $R_0$ are the constants obtained from a first calibration as described in FIG. 3. $G_{i,SS}$, $C_{EP}$ and $C_{G0}$ are constants to be determined by a second calibration for a specific location of an individual subject within a specific time period. In one embodiment, they are determined by applying techniques such as multiple linear regressions, partial least squares regression or other techniques using a calibration dataset containing the variables: $C_G$, $S_i$, and r (or z). The blood glucose concentration $C_G$ is determined by equation (21)

based on the absolute Raman ratio r and the measured Raman intensity $S_i$, both of which can be retrieved from the same Raman spectrum obtained from a certain body location.

Approach 4 Based on Relative Raman Ratio

On the other hand, the Raman ratio for the skin thickness in equation (7) can be rewritten as $$r_0 + \Delta r = R_{EP}\left(1 - e^{-\frac{2(z_0+\Delta z)}{\lambda}}\right) + R_0 \quad (22)$$

with $r_0$ defined as $$r_0 = R_{EP}\left(1 - e^{-\frac{2z_0}{\lambda}}\right) + R_0 \quad (23)$$

where $z_0$ is the mean epidermis thickness and $r_0$ is the corresponding mean Raman ratio, both are constants. Within a small body region, $\Delta \ll \lambda$. By first order approximation, $$e^{-\frac{2(z_0+\Delta z)}{\lambda}} = e^{-\frac{2z_0}{\lambda}}\left(1 - \frac{2\Delta z}{\lambda}\right) \quad (24)$$

Substituting equation (24) into equation (22), then:

$$\Delta z = \frac{\lambda}{2R_{EP}}\left(e^{\frac{2z_0}{\lambda}}\right)\Delta r \quad (25)$$

Substituting equation (25) into equation (19), then:

$$C_G = C_0 + \Sigma_i C_{i,S} S_i + \Sigma_i C_{i,Sr}(S_i \Delta r) + C_r \Delta r \quad (26)$$

where $$C_{i,Sr} = \frac{\lambda}{2R_{EP}}\left(e^{\frac{2z_0}{\lambda}}\right)C_{i,SZ} \text{ and } C_r = \frac{\lambda}{2R_{EP}}\left(e^{\frac{2z_0}{\lambda}}\right)C_z \quad (27)$$

$C_0$, $C_{i,S}$, $C_{i,Sr}$, and $C_r$ are constants to be determined by a second calibration for a specific location of an individual subject within a specific time period. In one embodiment, they are determined by applying techniques such as multiple linear regressions, partial least squares regression or other techniques using a calibration dataset containing the variables: $C_G$, $S_i$, and $\Delta r$.

Figure 6:
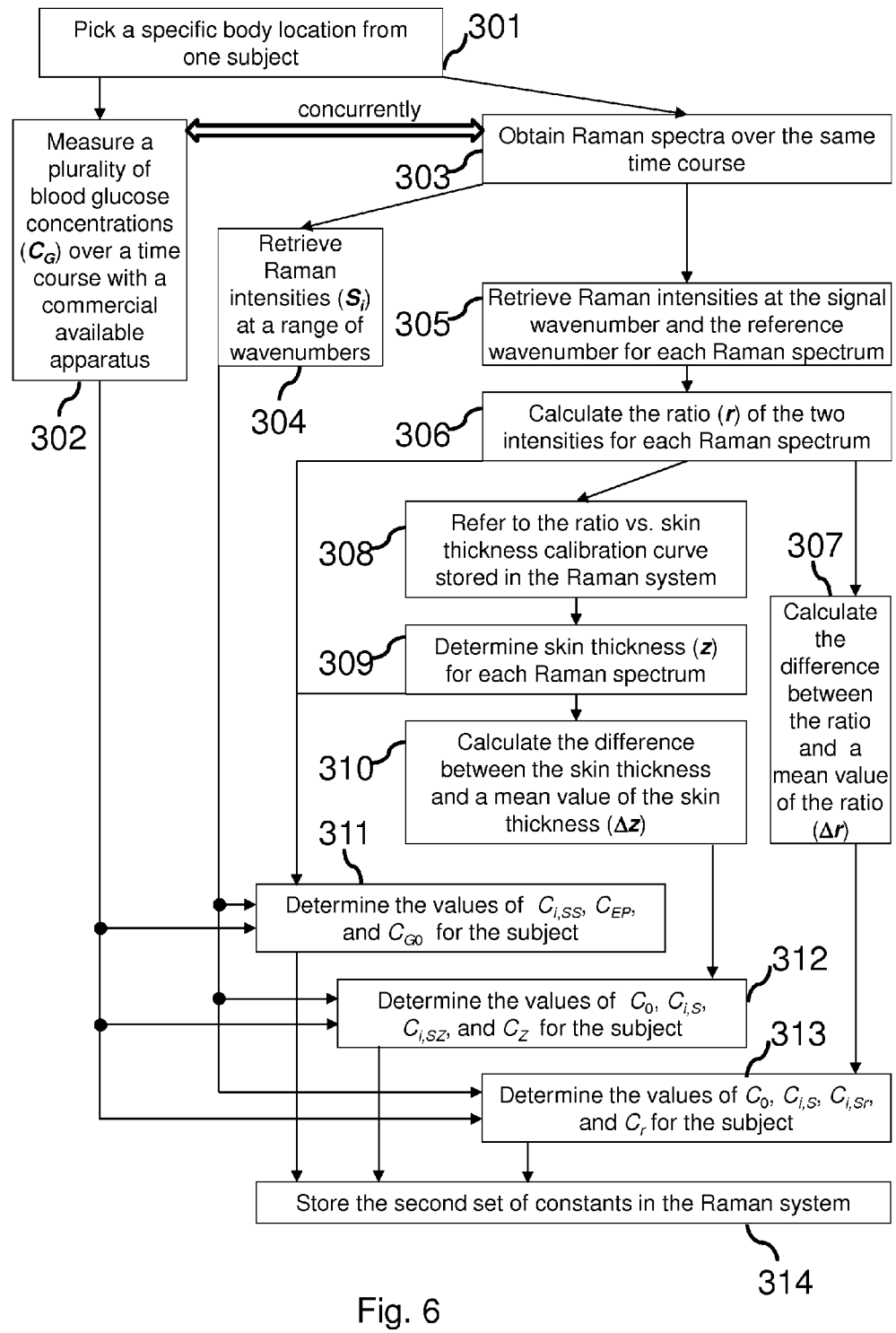
FIG. 6 is a flow chart for the second calibration procedures according to an embodiment of the present invention.

In an exemplary embodiment, a flow chart for the second calibration procedure is shown in FIG. 6. As discussed previously, the constants that need to be calibrated in each of the four approaches are different. For Approach 1 and 3, $C_{i,SS}$, $C_{EP}$ and $C_{G0}$ are needed. The constants for Approach 2 are $C_0$, $C_{i,S}$, $C_{i,SZ}$, and $C_Z$ and those for Approach 4 are $C_0$, $C_{i,S}$, $C_{i,Sr}$, and $C_r$. These different groups of constants, or any combination of them, are all referred to as second set of constants. In one embodiment, the second calibration procedure determines all the constants required for all these four approaches. The details of the procedure are as follows: First, a subject is picked in step 301 and given a standard glucose solution drink. Blood glucose measurements are taken by a commercially available glucose meter every 15 minutes from the subject in step 302. Concurrently, in step 303, Raman spectra are collected over the same time course from the subject by the Raman system of the present invention. Then, Raman intensities at a range of wavenumbers between 800 cm$^{-1}$-1500 cm$^{-1}$ are retrieved for each spectrum in step 304. After that, Raman intensities at the signal wavenumber and the reference wavenumber are retrieved from each Raman spectrum in step 305. Then, the ratio of the two intensities for each Raman spectrum is calculated in step 306. Then, in step 307 the difference between the Raman ratio r for the skin thickness and a pre-determined Raman ratio mean value $r_0$ for the skin thickness is calculated from all calibration Raman spectra. This protocol produced a set of skin Raman spectra with corresponding reference blood glucose values $C_G$. From each Raman spectrum, both Raman intensity $S_i$ at certain wavenumbers and relative Raman ratio $\Delta r$ can be retrieved ($\Delta r$ is calculated by subtracting r by the Raman ratio mean value $r_0$ (described below)). Finally in step 313, the values of $C_0$, $C_{i,S}$, $C_{i,Sr}$, and $C_r$ are determined using the aforementioned multivariate model described in equation (26) for Approach 4 based on relative Raman ratio with the variables: $C_G$, $S_i$, and $\Delta r$. To determine the value of the constants in Approach 1, 2 and 3, the same steps from step 301 to step 306 shown in FIG. 6 applies. Following step 306, the skin thickness z is determined in step 309 by referring to the ratio vs. skin thickness calibration curve stored in the Raman system in step 308. Then the difference between the skin thickness and a pre-determined skin thickness mean value is calculated in step 310 to obtain $\Delta z$ ($\Delta z$ is calculated by subtracting z by the skin thickness mean value $z_0$ (described below)). This protocol produced a set of skin Raman spectra with corresponding reference blood glucose values $C_G$. From each Raman spectrum, both Raman intensity $S_i$ at certain wavenumbers and absolute skin thickness z (Approach 1) or absolute Raman ratio r (Approach 3) or relative skin thickness $\Delta z$ (Approach 2) can be retrieved. In step 311, the values of $C_{i,ss}$, $C_{EP}$, and $C_{G0}$ are determined based on the aforementioned multivariate model described in equation (16) with the variables: $C_G$, $S_i$, and z, or equation (21) with the variables $C_G$, $S_i$, and r. In step 312, the values of $C_0$, $C_{i,S}$, $C_{i,SZ}$, and $C_Z$ are determined based on the aforementioned multivariate model described in equation (19) with the variables: $C_G$, $S_i$, and $\Delta z$. Finally in step 314, the second set of constants are stored in the Raman system.

In one embodiment, $r_0$ is pre-determined Raman ratio mean value by averaging at least two values of the Raman ratio r for the skin thickness obtained from substantially same body location from the same subject.

In a further embodiment, $z_0$ is pre-determined skin thickness mean value by averaging at least two values of skin thickness obtained from substantially same body location from the same subject. In another embodiment, an external reference source is used to determine the value of $z_0$ at the same body location.

Figure 7:
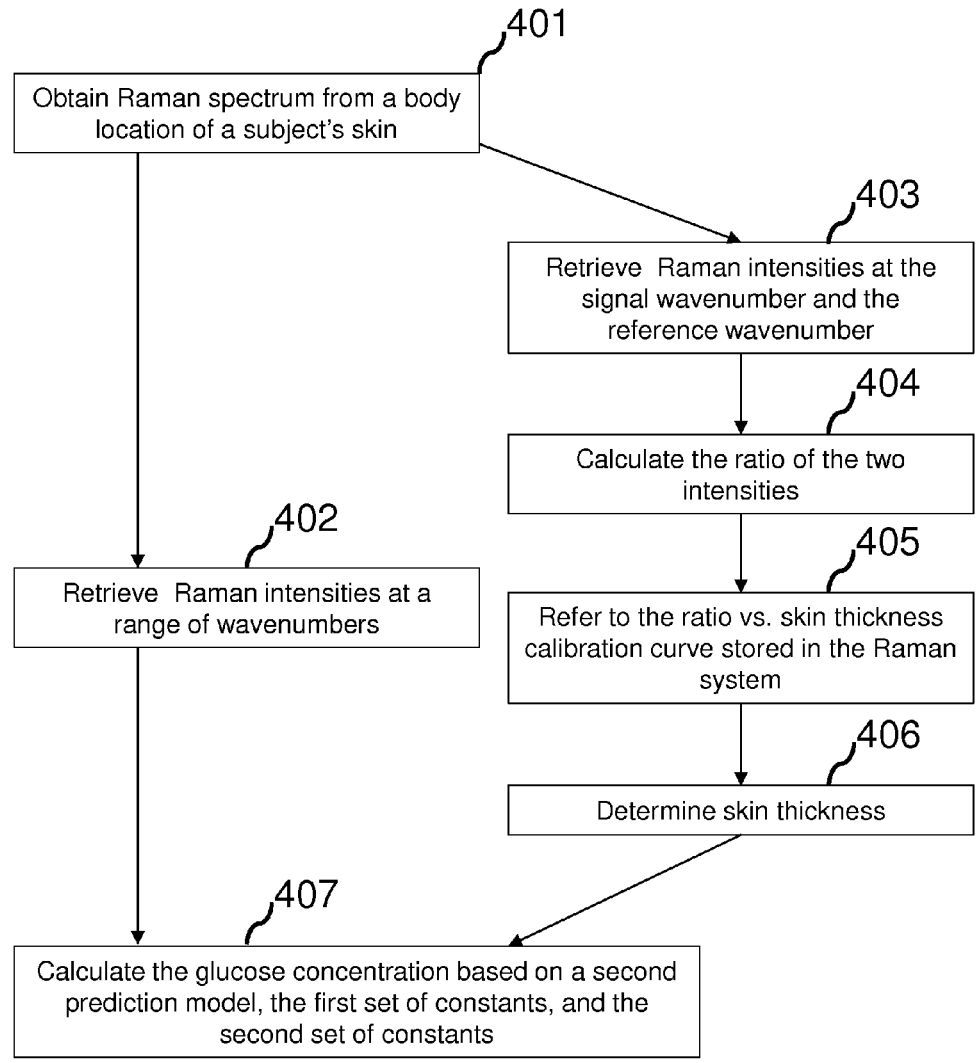
FIG. 7 is a flow chart for Approach 1 to determining blood glucose concentration according to an embodiment of the present invention based on absolute skin thickness.

In an exemplary embodiment, a flow chart for Approach 1 to determining blood glucose concentration based on absolute skin thickness is shown in FIG. 7. In step 401, Raman spectrum from a target body location is obtained by the Raman system of the present invention. Then, Raman intensities at a range of wavenumbers between 800 cm$^{-1}$-1500 cm$^{-1}$ are retrieved from the Raman spectrum in step 402. Raman intensities at the signal wavenumber and the reference wavenumber are retrieved from the Raman spectrum in step 403. After that, the ratio of the two intensities is calculated in step 404 and the skin thickness is determined in step 406 by referring to the predetermined ratio vs. skin thickness calibration curve stored in the Raman system in step 405. Finally in step 407, the second prediction model described in equation (16) is applied to calculate the blood glucose concentration.

Figure 8:
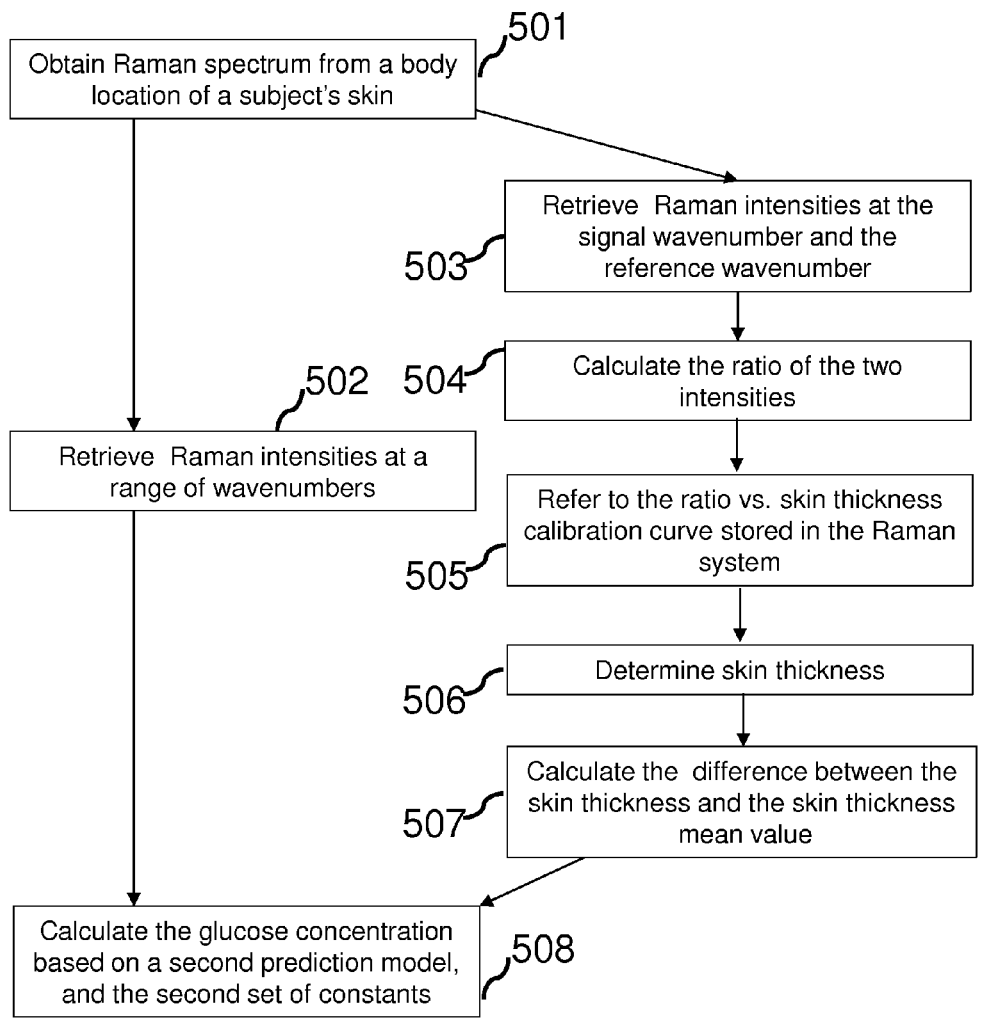
FIG. 8 is a flow chart for Approach 2 to determining blood glucose concentration according to an embodiment of the present invention based on relative skin thickness.

In an exemplary embodiment, a flow chart for Approach 2 of determining blood glucose concentration based on relative skin thickness as describe in Approach 2 is shown in FIG. 8. After obtaining Raman spectrum from a target body location by the Raman system of the present invention in step 501, Raman intensities at a range of wavenumbers between 800 cm$^{-1}$-1500 cm$^{-1}$ are retrieved from the Raman spectrum in step 502. Then, the Raman intensities at the signal wavenumber and the reference wavenumber are retrieved from the Raman spectrum in step 503. After that, the ratio of the two intensities is calculated in step 504 and the skin thickness is determined in step 506 by referring to the predetermined ratio vs. skin thickness calibration curve stored in the Raman system in step 505. In step 507, the difference between the skin thickness and a pre-determined skin thickness mean value ($z_0$) is calculated to obtain $\Delta z$. Finally in step 508, the second prediction model described in equation (19) based on relative skin thickness is applied to calculate the blood glucose concentration. In essence, each subject has a pre-calibrated dataset comprising values of $C_0$, $C_{i,S}$, $C_{i,SZ}$, $C_Z$ and $z_0$. The blood glucose concentration $C_G$ of each subject is determined by equation (19) based on skin thickness z and Raman intensity $S_i$, both of which are retrieved from the same Raman spectrum obtained from a target body location on the subject.

In another exemplary embodiment, blood glucose concentration is determined based on absolute Raman ratio as described in Approach 3. First, Raman spectrum from a target body location is obtained by the Raman system of the present invention. Then, Raman intensities at a range of wavenumbers between 800 cm$^{-1}$-1500 cm$^{-1}$ as well as at the signal wavenumber and the reference wavenumber are retrieved from the Raman spectrum. After that, the ratio of the two intensities at the signal wavenumber and the reference wavenumber is calculated. Finally, the second prediction model using equation (21) is applied to calculate the blood glucose concentration.

In a further exemplary embodiment, blood glucose concentration is determined based on relative Raman ratio as described in Approach 4. After obtaining Raman spectrum from a target body location by the Raman system of the present invention, Raman intensities at a range of wavenumbers between 800 cm$^{-1}$-1500 cm$^{-1}$ are retrieved from the Raman spectrum. Then, the Raman intensities at the signal wavenumber and the reference wavenumber are retrieved from the Raman spectrum. After that, the ratio of the two intensities is calculated; the difference between the Raman ratio and a pre-determined mean value of the Raman ratio ($r_0$) is calculated to obtain $\Delta r$. Finally, the second prediction model using equation (26) based on relative Raman ratio is applied to calculate the blood glucose concentration. In essence, each subject has a pre-calibrated dataset comprising values of $C_0$, $C_{i,S}$, $C_{i,SZ}$, $C_Z$ and $z_0$. The blood glucose concentration $C_G$ of each subject is determined by equation (26) based on Raman ratio r and Raman intensity $S_i$, both of which are retrieved from the same Raman spectrum obtained from a target body location on the subject.

EXPERIMENTAL RESULTS

Figure 9:
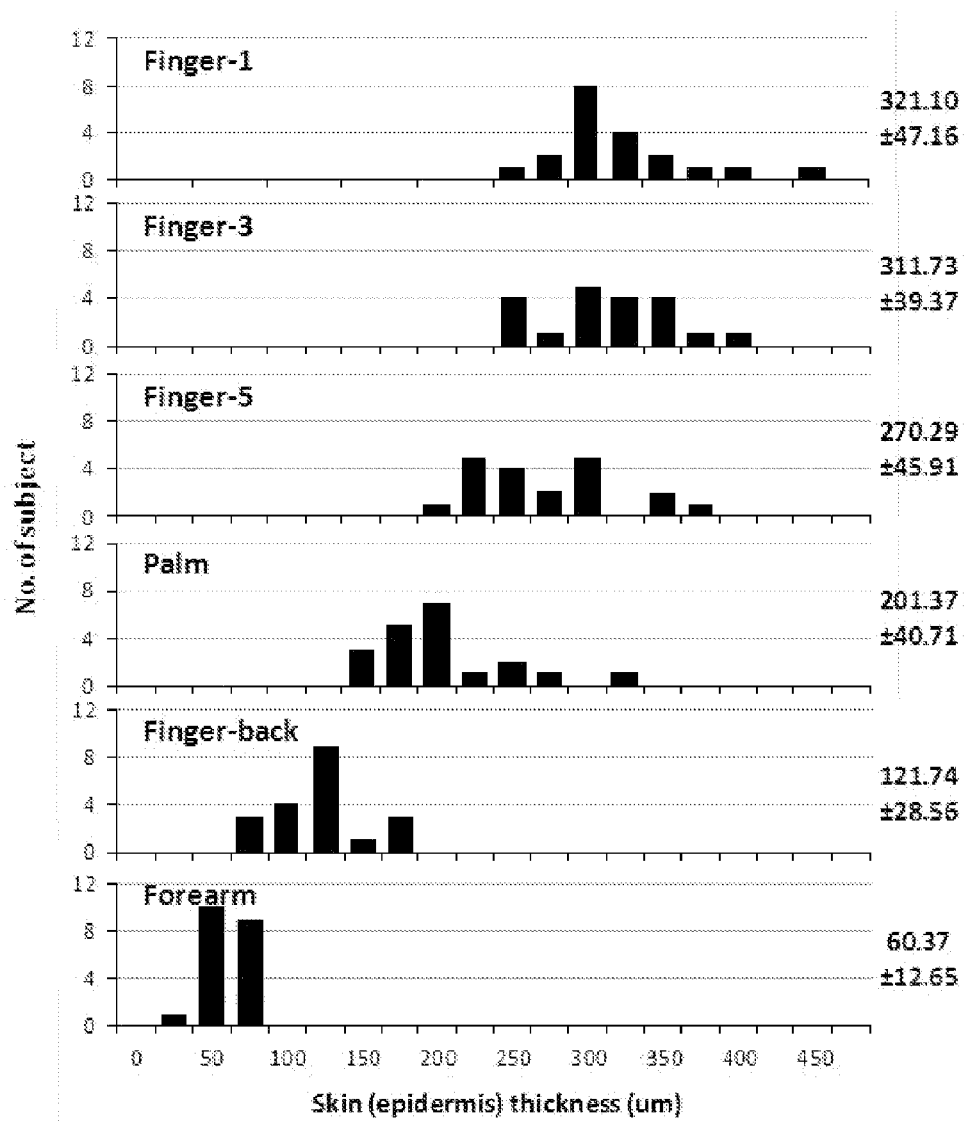
FIG. 9 is a plot of the predicted skin thickness according to the present invention for twenty subjects at six different locations.
Figure 10A:
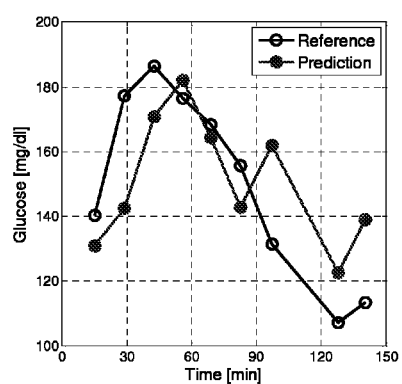
FIG. 10A shows time-domain plots of predicted blood glucose concentration and reference blood glucose concentration when the variation of skin thickness is not considered.
Figure 10B:
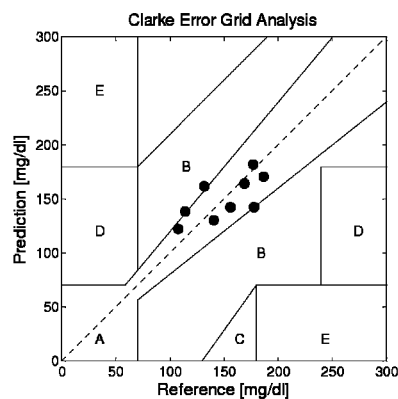
FIG. 10B is the corresponding Clarke Error Grid plot.
Figure 10C:
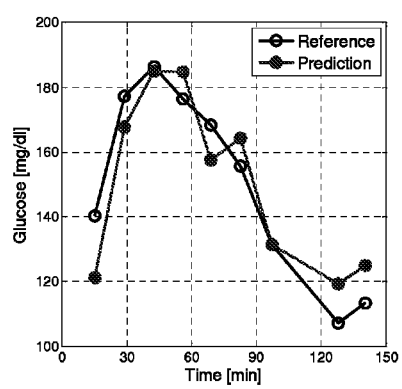
FIG. 10C shows time-domain plots of predicted blood glucose concentration and reference blood glucose concentration with the variation of skin thickness compensated according to the approach disclosed in the present invention.
Figure 10D:
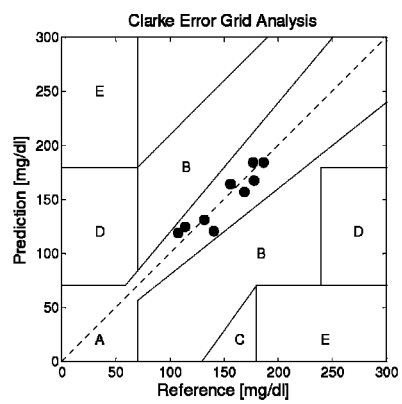
FIG. 10D is the corresponding Clarke Error Grid plot.

An experiment was performed among twenty volunteers aged from 22-45 (15 males and 5 females). Skin thickness of each subject was measured by the Raman system described in the present invention. Each measurement was taken at six different body locations: the thumb tip (Finger-1), the middle finger tip (Finger-3), the little finger tip (Finger-5), the thenar (Palm), the posterior surface of the mid finger at the medial phalange (Finger-back), and the anterior surface of the forearm (Forearm). For each Raman spectrum obtained from each body location, the ratio of Raman intensity at 1321 cm$^{-1}$ and 1446 cm$^{-1}$ was calculated. Then skin thickness of each body location on each subject was predicted by referring to the ratio vs. skin thickness calibration curve stored in the Raman system. Skin thickness distribution for the twenty subjects at each abovementioned body locations are summarized in FIG. 9. The x-axis is the skin thickness predicted by the present invention. The y-axis is the number of subjects. The mean value of predicted skin thickness of epidermis at Finger-1, Finger-3, Finger-5, Palm, Finger-back, and Forearm are 321 μm, 312 μm, 270 μm, 201 μm, 122 μm, and 60 μm, respectively. The standard deviation of predicted skin thickness of epidermis for these six body locations are 47 μm, 39 μm, 46 μm, 41 μm, 29 μm, and 13 μm, respectively. The result is consistent with those obtained with other means of skin thickness measurement in the previous studies, e.g., H. Fruhstorfer, et al, Clinical Anatomy, 2000, Vol. 13(6), pp. 429-433; M. J. Koehler, et al, Skin Research and Technology, 2010, Vol. 16(3), pp. 259-264; S. S. Huang, Chinese Journal of Medical Aesthetics and Cosmetology, 2011, Vol. 17(1), pp. 34-36; K. Robertson, Acta dermato-venereologica, 2010, Vol. 90(4), pp. 368-373. It clearly demonstrates the feasibility of determining skin thickness based on Raman spectrum and the first prediction model.

Another experiment was performed on a male subject to compare the predicted blood glucose concentration with the reference value obtained by a commercially available glucose meter. The predicted blood glucose concentration was obtained by Approach 4 of the present invention based on relative Raman ratio. A calibration was performed on the subject to pre-store the values of $C_0$, $C_{i,S}$, $C_{i,Sr}$, and $C_r$ in the Raman system. The subject was given a glucose solution drink containing 68 g glucose after at least 8 hours of fasting. Over the time course of approximately two hours, Raman spectra were collected every 15 minutes from the anterior surface of the forearm of the subject using the Raman system described herein. In this embodiment, the excitation light source was a 450 mW 1064 nm continuous wave laser and the detector was an InGaAs CCD array. The acquisition time was 100 sec. From each Raman spectrum, both Raman intensity $S_i$ at certain wavenumbers and relative Raman ratio $\Delta r$ were retrieved according to the present invention. Then blood glucose concentration was predicted by applying the second prediction model as described by equation (26) stored in the Raman system. For comparison, the predicted glucose concentration without considering the variation of skin thickness was also calculated using the same equation (26) with $\Delta r=0$. Concurrently, reference blood glucose concentrations were measured by taking the blood drops from the finger tip of the subject using a commercially available blood glucose meter every 15 minutes. In FIGS. 10 (a) & (b), the predicted glucose concentration without considering the variation of skin thickness (i.e. $\Delta r=0$) and the reference glucose concentration are plotted. The root mean square error (RMSE) of the prediction is 20 mg/dl, the mean absolute relative difference (MARD) is 12%, and the correlation coefficient ($r_{xy}$) is 0.68. In FIGS. 10 (c) & (d), the predicted glucose concentration with considering the variation of skin thickness (i.e. $\Delta r \neq 0$) and the reference glucose concentration become closer. The root mean square error of the prediction is 11 mg/dl, the mean absolute relative difference is 6%, and the correlation coefficient is 0.92. The experiment results on the subject clearly demonstrate the feasibility of determining blood glucose concentration based on Raman spectrum and the second prediction model.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein. For example, the ratio vs. skin thickness calibration curve can be further customized by the age, gender, and ethnicity of the subjects. For another example, in the model for glucose prediction, the first layer and the second layer are not limited to epidermis and dermis, e.g., in some cases, they could refer to the upper layer of epidermis (which is dry) and the lower layer of epidermis (which contains some glucose). And the glucose concentration in the first layer is not necessary zero. In general, one may consider two layers of skin, the top one has low volume fraction of interstitial fluid giving lower glucose contents, while the bottom one has high volume fraction of interstitial fluid giving higher glucose contents. The equations (19) and (26) can still be applied for glucose prediction. As the second set of constants in these equations are obtained from the calibration process, they might deviate from the definition in the equations (20) and (27). And such deviations compensate the deviations from the simplified model to the real skin been measured. Therefore, the glucose prediction method disclosed in this invention is not limited to our aforementioned simplified model.

Furthermore, it is mentioned in previous paragraphs that the second calibration procedure computes all the constants for all the four approaches. This may not be necessary if one has decided which of the four approaches to take, since only those constants required by that selected approach are required for calibration. For example, if Approach 4 is chosen, only $C_0$, $C_{i,S}$, $C_{i,Sr}$, and $C_r$ are needed to be obtained from the second calibration. Other constants such as $C_{i,SS}$, $C_{EP}$, $C_{G0}$, $C_{i,SZ}$ and $C_Z$ are not needed.

What is claimed is:

1. A method of operating a physiological measurement system for measuring a concentration of glucose in the blood of a subject comprising the steps of:
   a) receiving a Raman signal from a predetermined area of said subject's skin; said skin comprising at least a first layer and a second layer;
   b) obtaining a first data relating to the thickness of said first layer;
   c) acquiring a second data relating to the glucose concentration within said second layer based on said Raman signal; and
   d) determining said concentration of glucose in the blood of said subject based on said first data and said second data,
   wherein said step of obtaining said first data further comprises the steps of:
   measuring a first intensity of said Raman signal at a first predetermined wavenumber and a second intensity of said Raman signal at a second predetermined wavenumber;
   calculating a ratio of said first intensity and said second intensity; and
   deriving said first data based on said ratio and a first prediction model.

2. The method of claim 1, wherein said first predetermined wavenumber is selected from a spectral range of 1300 cm$^{-1}$ to 1340 cm$^{-1}$; and said second predetermined wavenumber is selected from a spectral range of 1440 cm$^{-1}$ to 1460 cm$^{-1}$.

3. The method of claim 1, wherein said first prediction model satisfies the equation $$r = R_{EP}(1 - e^{-\frac{2z}{\lambda}}) + R_0$$

where r is said ratio of said first intensity and said second intensity, $R_{EP}$, $\lambda$ and $R_0$ are a first set of constants obtained from a first calibration, and z is said first data relating to said thickness of said first layer.

4. The method of claim 3, wherein said first calibration comprises steps of:
   a) collecting a plurality of said ratios at different body locations of at least one subject;
   b) measuring skin thickness for each said different body location by a reference method;
   c) generating a calibration curve correlating said ratio to said skin thickness for each said different body location; and
   d) determining said first set of constants from said calibration curve.

5. The method of claim 4, wherein said reference method is selected from an invasive method and a non-invasive method; said non-invasive method being selected from optical coherence tomography method, ultrasound imaging method, Terahertz imaging method, and near-infrared absorption.

6. The method of claim 4 wherein said determining step in claim 1 further comprises the step of computing said concentration of glucose in the blood of said subject based on said first data, said second data and a second prediction model.

7. The method of claim 6 wherein said second prediction model further comprising a second set of constants which are determined by a second calibration.

8. The method of claim 7, wherein said second data is at least one intensity of said Raman signal and said second prediction model satisfies the equation $$C_G = \sum_i C_{i,SS} S_i (e^{\frac{2z}{\lambda}}) + C_{EP}(e^{\frac{2z}{\lambda}} - 1) + C_{G0}(e^{\frac{2z}{\lambda}})$$

wherein $C_G$ is said concentration of glucose in the blood, $S_i$ is said intensity of said Raman signal, z is said thickness of said first layer, $\lambda$ is a constant parameter in said first set of constants, $C_{i,SS}$, $C_{EP}$ and $C_{G0}$ are said second set of constants.

9. The method of claim 7, wherein said second data is at least one intensity of said Raman signal and said second prediction model satisfies the equation $$C_G = C_0 + \sum_i C_{i,S} S_i + \sum_i C_{i,SZ}(S_i \Delta z) + C_Z \Delta z$$

wherein $C_G$ is said concentration of glucose in the blood, $S_i$ is said intensity of said Raman signal, $\Delta z$ is a relative skin thickness being a difference between said thickness of said first layer and a skin thickness mean value, $C_0$, $C_{i,S}$, $C_{i,SZ}$, and $C_Z$ are said second set of constants.

10. The method of claim 9, wherein said skin thickness mean value is obtained by averaging at least two values of skin thickness obtained from substantially same body location of same subject.

11. The method of claim 7, wherein said second data is at least one intensity of said Raman signal and said second prediction model satisfies the equation $$C_G = \sum_i C_{i,SS} S_i \left( \frac{R_{EP}}{R_{EP}+R_0-r} \right) + C_{EP} \left( \frac{r-R_0}{R_{EP}+R_0-r} \right) + C_{G0} \left( \frac{R_{EP}}{R_{EP}+R_0-r} \right)$$

wherein $C_G$ is said concentration of glucose in the blood, $S_i$ is said intensity of said Raman signal, r is said ratio, $R_{EP}$ and $R_0$ are constant parameters in said first set of constants, $C_{i,SS}$, $C_{EP}$ and $C_{G0}$ are said second set of constants.

12. The method of claim 7, wherein said second data is at least one intensity of said Raman signal and said second prediction model satisfies the equation $$C_G = C_0 + \sum_i C_{i,S} S_i + \sum_i C_{i,Sr}(S_i \Delta r) + C_r \Delta r$$

wherein $C_G$ is said concentration of glucose in the blood, $S_i$ is said intensity of said Raman signal, $\Delta r$ is a relative Raman ratio being a difference between said ratio and a Raman ratio mean value, $C_0$, $C_{i,S}$, $C_{i,Sr}$, and $C_r$ are said second set of constants.

13. The method of claim 12, wherein said Raman ratio mean value is obtained by averaging at least two values of Raman ratio for the skin thickness obtained from substantially same body location of same subject.

14. The method of claim 7, wherein said second calibration comprises steps of:
 a) measuring a plurality of blood glucose concentrations over a time course at a predetermined body location from same subject by a second reference method;
 b) concurrently, collecting a plurality of Raman spectra from said predetermined body location of said same subject;
 c) deriving at least one group of variables from each said Raman spectrum; and
 d) determining said second set of constants for said subject based on said second prediction model using said plurality of blood glucose concentration and said group of variables.

15. The method of claim 14, wherein said at least one group of variables is chosen from at least one intensity of said Raman signal, said ratio, a relative Raman ratio, said thickness of said first layer, a relative skin thickness and any combination therefrom.

16. The method of claim 14, wherein said second set of constants is obtained through partial least squares regression.

17. A physiological measurement system for measuring physiological data of a subject at a predetermined area of said subject's skin comprising:
 a) a Raman spectroscopic unit comprises
  (i) an excitation light source that illuminates an optical signal into said predetermined area of said subject's skin, said subject's skin further comprising a first layer and a second layer; and
  (ii) an optical detector that receives a Raman signal reflected from said predetermined area of said subject's skin; and
 b) a signal processing unit comprises
  (i) a microprocessor coupled to said optical detector;
  (ii) a non-transitory computer-readable storage medium coupled to said microprocessor, said computer-readable storage medium encoded with computer-readable codes to instruct said microprocessor to execute the following steps:
   i. acquiring a first data relating to the skin thickness of said first layer from said Raman signal;
   ii. acquiring a second data relating to the glucose concentration within said second layer from said Raman signal;
   iii. computing said skin thickness of said first layer based on said first data; and
   iv. computing said glucose concentration of said second layer based on said skin thickness of said first layer, said second data, and a second prediction model,
 wherein said step of acquiring said first data further comprises the steps of:
 measuring a first intensity of said Raman signal at a first predetermined wavenumber and a second intensity of said Raman signal at a second predetermined wavenumber;
 calculating a ratio of said first intensity and said second intensity; and
 deriving said first data based on said ratio and a first prediction model.

18. A method of operating a physiological measurement system for measuring the thickness of a predetermined area of a subject's skin; said method comprising the steps of:
 a) receiving an Raman signal from said predetermined area; said Raman signal comprising a plurality of signal components, each said signal component identified by a wavenumber thus forming a composite Raman spectrum;
 b) identifying a first predetermined wavenumber and a second predetermined wavenumber from said Raman signal;
 c) retrieving a first intensity of said Raman signal at said first predetermined wavenumber and a second intensity of said Raman signal at said second predetermined wavenumber;
 d) calculating a ratio of said first intensity and said second intensity; and
 e) determining the thickness of said predetermined area of said subject's skin based on said ratio and a first prediction model,
 wherein said first prediction model comprises a functional relationship among a plurality of attributes correlating the thickness of said predetermined area and said ratio.

19. The method of claim 18, wherein said functional relationship is:

$$r = R_{EP}(1 - e^{-\frac{2z}{\lambda}}) + R_0$$

where r is said ratio of said first intensity and said second intensity, $R_{EP}$, $\lambda$ and $R_0$ are constants obtained from a first calibration, and z is the thickness of said predetermined area of said subject's skin.

20. The method of claim 18, wherein said first calibration comprises steps of:
   a) collecting a plurality of said ratios at different locations of at least one subject;
   b) measuring skin thickness for each said different location by a reference method; and
   c) generating a calibration curve correlating said ratio to said skin thickness for each said different location.

21. The method of claim 18, wherein said first predetermined wavenumber and said second predetermined wavenumber are determined by:
   a) measuring a plurality of skin thicknesses at a plurality of body locations from a plurality of subjects by said reference method;
   b) obtaining the corresponding Raman spectrum of each said body location; said Raman spectrum comprising a plurality of signal with wavenumber ranging from 300 $cm^{-1}$ to 1800 $cm^{-1}$;
   c) selecting a first set of wavenumbers sensitive to skin characteristic composition of said body locations and a second set of wavenumbers insensitive to skin characteristic composition of said body locations;
   d) selecting a first wavenumber from said first set and a second wavenumber from said second set;
   e) retrieving a first intensity from said Raman spectrum at said first wavenumber and a second intensity from said Raman spectrum at said second wavenumber;
   f) calculating a Raman ratio of said first intensity and said second intensity for each Raman spectrum;
   g) repeating step d-f for all combinations of said first wavenumber and said second wavenumber;
   h) for each said first wavenumber and each said second wavenumber, identifying a set of candidate wavenumber pairs wherein in each said candidate wavenumber pair, said Raman ratios and said skin thicknesses of said plurality of subjects conform to a generic functional relationship as specified in said first prediction model;
   i) determining an optimal wavenumber pair among said set of candidate wavenumber pairs that yields most compact representation of said generic functional relationship; and
   j) assigning said first wavenumber and said second wavenumber in said optimal wavenumber pair as said first predetermined wavenumber and said second predetermined wavenumber respectively.

22. The method of claim 21 further comprises the steps of:
   a) for each said body location, identifying a cluster of points; each said point registering said Raman ratio and said skin thickness of a subject measured at said body location; and each cluster having a cluster center;
   b) retaining those candidate wavenumber pairs wherein said cluster centers at said body locations fit said generic functional relationship, and
   c) determining said optimal wavenumber pair as an candidate wavenumber pair among said candidate wavenumber pairs that yields minimum aggregated standard deviations of said clusters.

* * * * *